United States Patent
Miller et al.

(10) Patent No.: US 6,897,412 B1
(45) Date of Patent: May 24, 2005

(54) INWARD OPENING OVEN INTAKE FOR GAS CHROMATOGRAPHIC OVEN

(75) Inventors: Sammye Miller, New Castle, DE (US); Robert Rhodes, Lincoln University, PA (US); William Trescott, Wilmington, DE (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/764,463

(22) Filed: Jan. 27, 2004

(51) Int. Cl.[7] .................................................. A21B 1/00
(52) U.S. Cl. ...................... 219/400; 210/175; 210/179; 432/48
(58) Field of Search .................. 219/400; 210/175–179, 210/198.2; 432/48, 199

(56) References Cited

U.S. PATENT DOCUMENTS

| | | | | |
|---|---|---|---|---|
| 3,958,552 A | * | 5/1976 | Lawler | 126/21 A |
| 4,181,613 A | * | 1/1980 | Welsh et al. | 210/179 |
| 4,420,679 A | * | 12/1983 | Howe | 219/400 |
| 4,752,216 A | * | 6/1988 | Hurrell | 432/48 |
| 5,744,029 A | * | 4/1998 | Li et al. | 210/198.2 |

FOREIGN PATENT DOCUMENTS

JP        2002-14087        1/2002

* cited by examiner

Primary Examiner—Joseph Pelham

(57) ABSTRACT

An inward opening oven intake for a gas chromatographic (GC) oven includes an inward opening intake flap that opens into the GC oven near the bottom of the GC oven. Opening at a flap angle, the inward opening intake flap creates a low-pressure region to draw a large amount of airflow into the GC oven during cool-down. In addition, the inward opening oven intake manipulates the airflow within the GC oven to more efficiently draw heat away from the oven walls. This greater efficiency allows for faster cycle time and higher sample throughput.

20 Claims, 5 Drawing Sheets

INWARD OPENING OVEN INTAKE FOR GAS CHROMATOGRAPHIC OVEN

TECHNICAL FIELD

The technical field relates to a gas chromatographic oven, and, in particular, to oven cooling efficiency.

BACKGROUND

Gas chromatography (GC) is a physical method for the separation, identification, and quantification of chemical compounds. A sample mixture is injected into a flowing neutral carrier stream and the combination flows through a tube or chromatographic column. The inner surface of the column is coated or packed with a stationary phase. As the sample mixture and carrier stream flow through the column, the components within the mixture are retained by the stationary phase to varying degrees depending on the relative volatility of the individual components and on their respective affinities for the stationary phase. Different chemical compounds are retained for different times by the stationary phase. When the individual mixture components are released into the carrier stream by the stationary phase, the components are swept towards the column outlet to be detected and measured by a detector. The specific compounds in the components of the mixture can be identified and their relative concentrations determined by measuring peak retention times and peak areas respectively.

In the push for faster chromatography, the trend continues to be towards smaller, less thermally massive ovens. The oven temperature needs to be controlled at a specific rate. After one sample run is completed, the oven generally needs to be cooled down to the start temperature before another sample can be analyzed. To achieve faster cycle time and higher sample throughput, it is desirable to minimize the oven cool-down time. One method is to optimize the airflow into and within the oven both during heating and cooling. Engineering the airflow patterns is a challenge as visualization techniques are few and expensive. Most of the advances have been a result of trial and error.

Current solutions either passively or actively influence the airflow patterns into and within a GC oven during oven cool-down. For example, some GC ovens passively introduce fresh air into the oven by having the end of the intake duct situated directly behind the oven's stirring fan in a low-pressure region. This low-pressure region works to draw air in through the intake duct. With smaller GC ovens, a more active approach has been attempted to place the intake opposite the oven's stirring fan and to locate an additional boxer fan on the intake duct to force fresh air into the oven. A tradeoff exists in this design, however, because the boxer fan's placement forces the boxer fan to work against the oven's stirring fan. As a result, the stirring fan must be operated at only a percentage of its full power in order to not overwhelm the boxer fan during cooling.

SUMMARY

An air intake for an oven having an inside and an outside includes an intake duct; and a movable intake flap. The moveable intake flap is operably connected to the intake duct and has a closed and an open orientation. The intake flap is positioned so that when the intake flap is in the open orientation, more of the intake flap is located on the inside of the oven than on the outside of the oven. In the open orientation, the intake flap opens into the oven at a flap angle that creates a low-pressure region to draw airflow into the oven from the intake duct.

A method for providing an inward opening oven intake for a gas chromatographic oven includes assessing airflow inside an oven, determining an advantageous location for an intake flap, and placing the intake flap at the advantageous location near a bottom of the oven. The method further includes determining a flap angle of an opening of the intake flap, and enabling the intake flap to open into the oven at the flap angle to create a low-pressure region to assist in drawing airflow into the oven from one or more cooling fans.

A corresponding system for providing an inward opening oven intake for a gas chromatographic oven includes an intake duct positioned beneath an oven. The intake duct having one or more cooling fans. The system further includes an intake flap positioned at an advantageous location near a bottom of the oven. The intake flap opens into the oven at a flap angle to direct an airflow originating from the one or more cooling fans to approximate a direction of a second airflow originating from stirring fans inside the oven.

DESCRIPTION OF THE DRAWINGS

The preferred embodiments of a system and method for providing an inward opening oven intake for a gas chromatographic oven will be described in detail with reference to the following figures, in which like numerals refer to like elements, and wherein.

DETAILED DESCRIPTION

An inward opening oven intake for a gas chromatographic (GC) oven includes an inward opening intake flap that opens into the GC oven near the bottom of the GC oven. Opening at a flap angle, the inward opening intake flap creates a low-pressure region to draw a large amount of airflow into the GC oven during cool-down. In addition, the inward opening oven intake manipulates the airflow within the GC oven to more efficiently draw heat away from the oven walls. This greater efficiency allows for faster cycle time and higher sample throughput.

Figure 1:
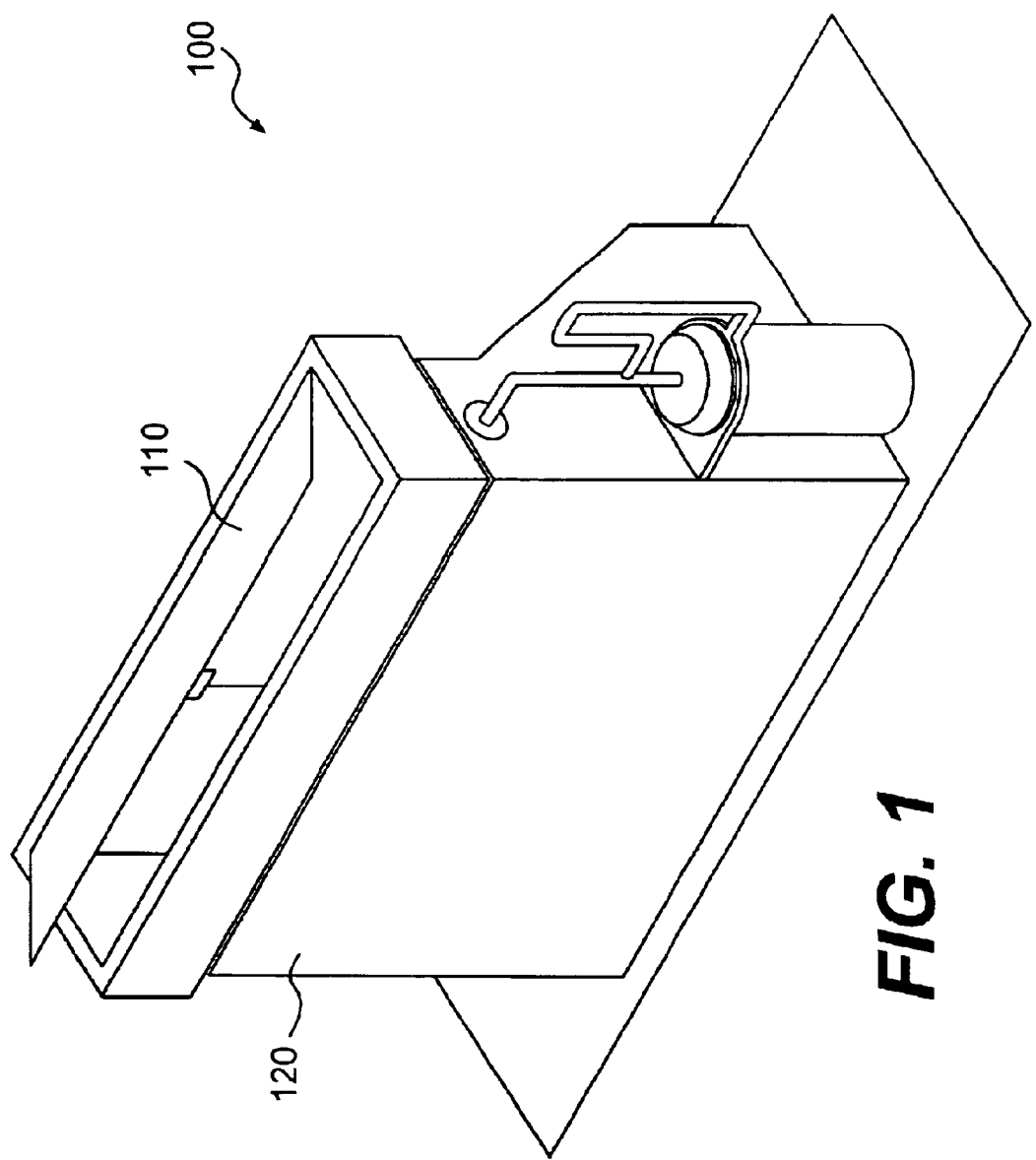
FIG. 1 illustrates an exemplary inward opening oven intake that includes an intake duct and an inward opening intake flap that opens into a gas chromatographic (GC) oven.
Figure 2:
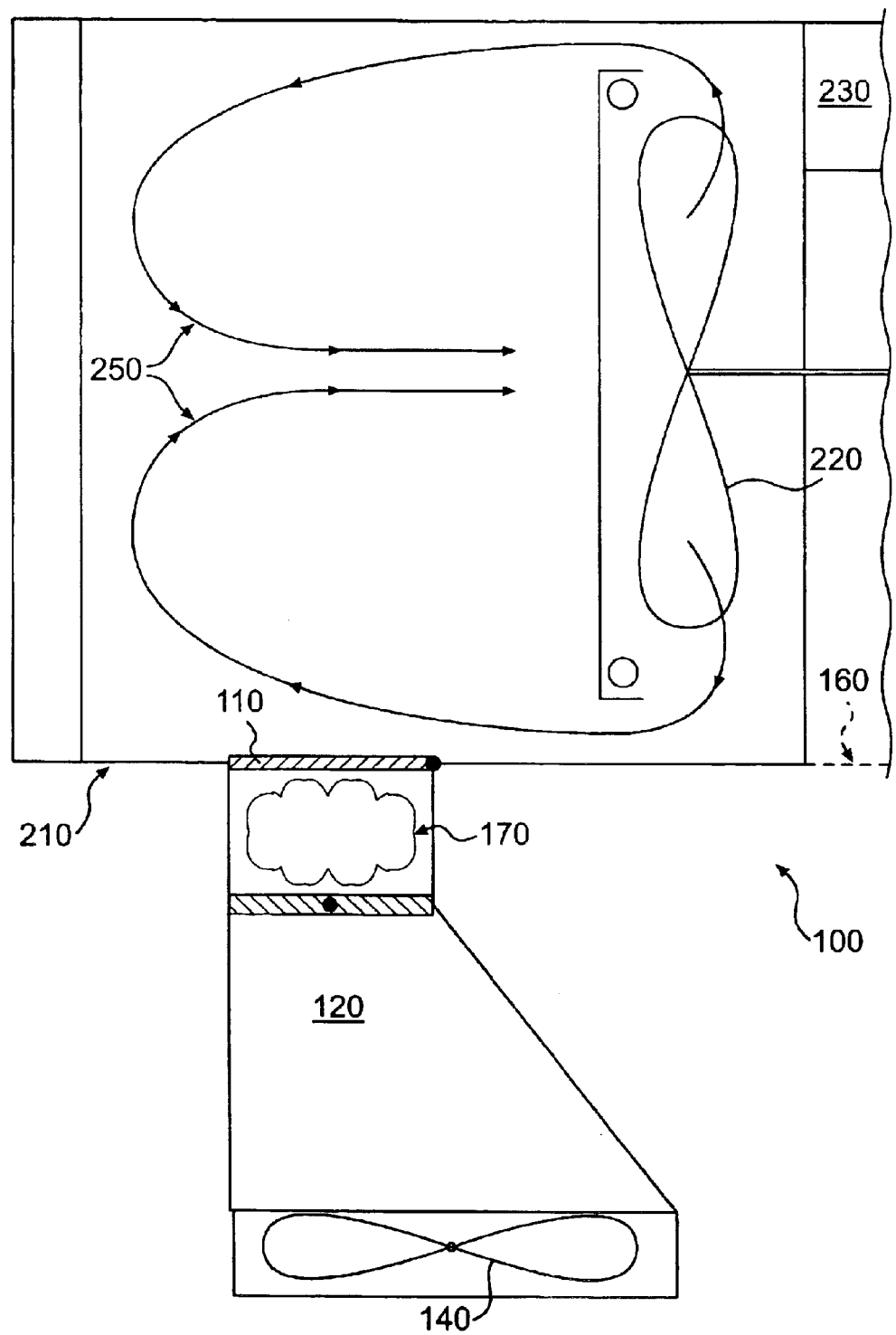
FIG. 2 illustrates a cutaway side view of the exemplary inward opening oven intake of FIG. 1 with the intake closed.
Figure 3:
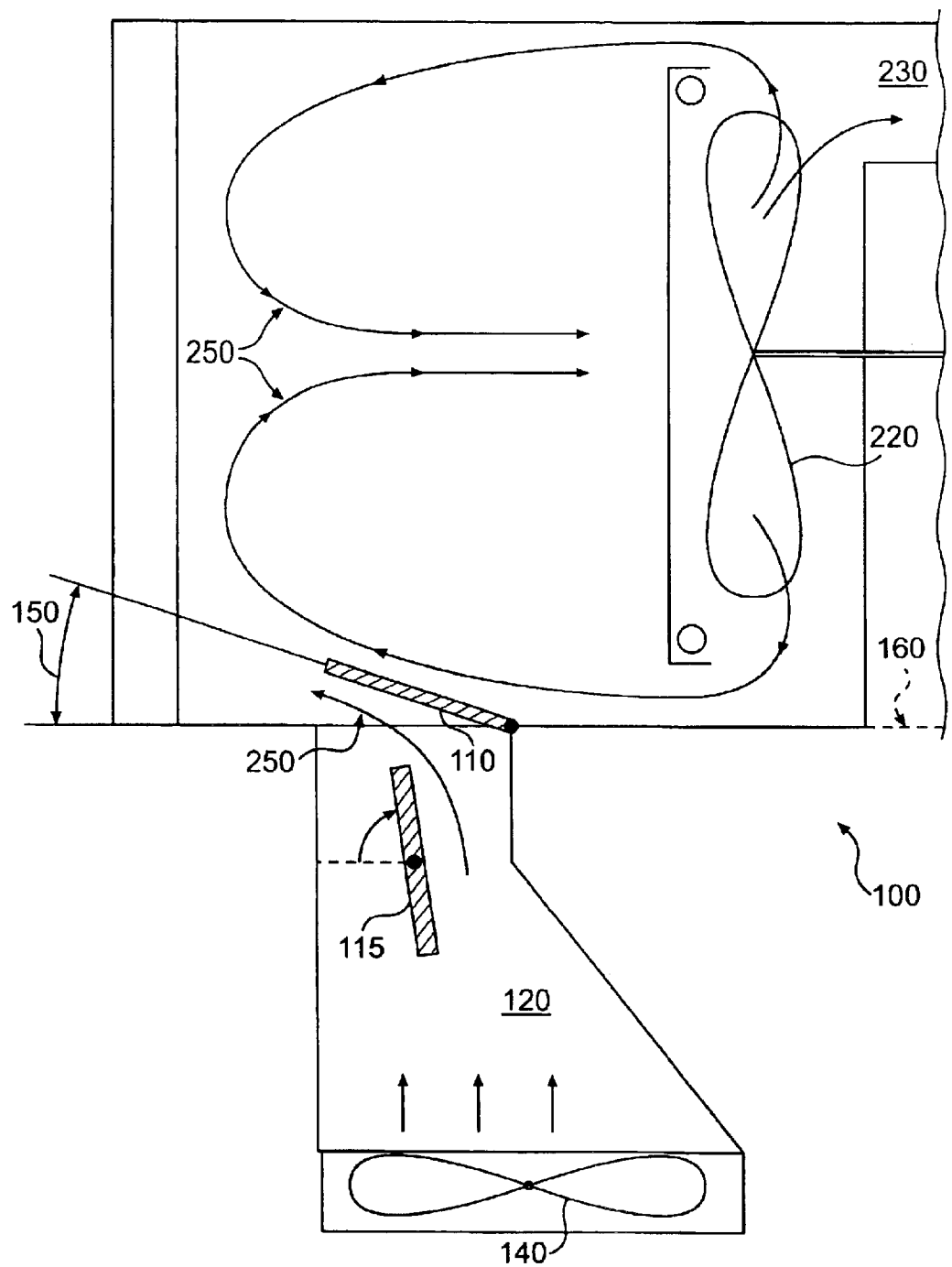
FIG. 3 illustrates a cutaway side view of the exemplary inward opening oven intake of FIG. 1 with the intake open.

FIG. 1 illustrates an exemplary inward opening oven intake 100 that includes an intake duct 120 and an inward opening intake flap 110 that opens into a GC oven 210 (shown in FIGS. 2 and 3). The intake duct 120 shown in FIG. 1 has a cross-section of approximately 165 mm×80 mm to accommodate 80 mm intake fans 140 (shown in FIGS. 2 and 3) that converges to a cross-section of 165 mm×35 mm to be minimally obtrusive to the oven 210. However, other shapes of intake duct can also be employed. The inward opening intake flap 110 shown in FIG. 1 has a long flat rectangular shape, approximately 165 mm×35 mm. However, other shapes of intake flap may be employed, such as a curved airfoil design. As shown in FIG. 1, the inward opening intake flap 110 opens into the GC oven 210. Generally, having a large obtrusive flap opening completely into the oven may cause disruption of airflow inside the GC oven 210 and is avoided. The inward opening intake flap 110 of FIG. 1 is long and thin, and only opens slightly into the GC oven 210 at a flap angle 150 (shown in FIG. 3). The shape, size and design of the inward opening intake flap 110 reduce interference with the airflow inside the GC oven 210.

FIG. 2 illustrates a cutaway side view of the exemplary inward opening oven intake 100 when the intake is closed. The inward opening intake flap 110 may open into the GC oven 210 at the bottom of the GC oven (at line 160). The GC oven 210 may include stirring fans 220 that provide airflow 250 inside the GC oven 210. The intake duct 120 may be located at the bottom of the GC oven 210 to fit smaller sized ovens. For example, this intake duct 120 is centered on the bottom of the oven 210 located about 5 mm from the oven door. The intake duct 120 may be made of stainless steel or aluminum material with either a uniform cross-section or a non-uniform cross-section.

The intake duct 120 may include one or more cooling fans 140. During cool-down, the inward opening intake flap 110 snaps open to allow air to flow from the cooling fans 140 through the intake duct 120 into the GC oven 210. The air then exhausts from the GC 210 oven into open space through an exhaust duct 230 (shown closed in FIG. 2). The inward opening intake flap 110 is closed in FIG. 2 but may open at a flap angle 150 (shown in FIG. 3) to approximate airflow 250 within the GC oven 210 such that air is more efficiently drawn out of the intake duct 120 into the GC oven 210.

FIG. 3 illustrates a cutaway side view of the exemplary inward opening oven intake 100 when the intake is open. During cool-down, the inward opening intake flap 110 snaps open into the GC oven 210 at a flap angle 150 generally between 0° and 90°. The cooling fans 140 in operation push fresh air upwards past the inward opening intake flap 110 into the GC oven 210.

The inward opening intake flap 110, opening at a flap angle 150, may direct the airflow 350 being introduced by the cooling fans 140 of the oven intake 100 to approximate the direction of the airflow 250 from the oven's stirring fans 220 to facilitate insertion of this cool flow 350. Also, the high velocity flow from the oven's stirring fans 220 flowing over the inward opening intake flap 110 creates a low-pressure region on top of the inward opening intake flap 110. The low-pressure region tends to draw additional airflow from other areas, such as from the oven intake 100, into the GC oven 210. This principle is referred to as Bernoulli's principle. As a result, in addition to the cooling fans 140 working to force air 350 into the GC oven 210, the airflow 250 inside the GC oven 210 creates a pressure to assist.

The flap opening angle 150 may be determined based on the angle of the airflow 250 originating from the stirring fans 220 flowing past the region where the inward opening intake flap 110 is located. To avoid disrupting the airflow 250 inside the GC oven 210, the flap angle 150 preferably approximates the angle of the airflow 250 flowing past the region where the inward opening intake flap 110 is located. A series of experiments with the inward opening intake flap 110 opening at different angles may be run to assess the airflow 250 inside any given GC oven 210 and to determine an advantageous location for the inward opening intake flap 110 and a flap angle 150 that results in the fastest cool-down. A flap angle 150 is usually specific to each oven design and may depend on the size and shape of the GC oven 210, the speed and location of the stirring fans 220, and the speed of the cooling fans 140 amongst several other parameters. The range of the flap angle may be between 0° and 90°. Some examples of the flap angle 150 are 30°, 40°, 50°, and 60°. For example, a 30° flap angle may be used for a small fast GC oven 210 without significantly disturbing the airflow 250 inside the GC oven 210 yet resulting in a faster cool-down.

Referring to FIG. 3, the oven intake 100 may optionally include a second flap 115. When the inward opening intake flap 110 opens at the flap angle 150, the second flap 115 may be positioned along the direction of the airflow 350 flowing from the cooling fans 140 to the GC oven 210. When the inward opening intake flap 110 snaps shut, the second flap 115 may swing 90° to provide a layer of air insulation 170 (shown in FIG. 2) between the GC oven 210 and the cooling fans 140, thus, insulating the cooling fans 140 from the hot oven 210.

The second flap may be connected to the inward opening intake flap 110 through a linkage system (not shown), such as a four-bar linkage system. A four-bar linkage system is a mechanism that consists exclusively of "revolute" joints. The linkage system may be controlled by a control device, such as a solenoid (shown in FIG. 4). The control device may open the flaps 110, 115 at different pre-defined angles. For example, the linkage system may drive the second flap 115 90° and the inward opening intake flap a flap angle 150 less than 90°. Other methods of moving the flaps 110, 115, such as a stepper motor, a proportional solenoid, or other types of proportional control device, may be employed. The proportional control device may allow the flaps 110, 115 to close more softly and therefore not upset the thermal equilibrium in the oven as much. In the event of unexpected power loss, the control device may function as a switch and cause the flaps 110, 115 to automatically snap shut to keep the oven and the cooling fans separate during the power loss. Alternatively, the second flap 115 may have its own control device, mechanical or otherwise.

Figure 4:
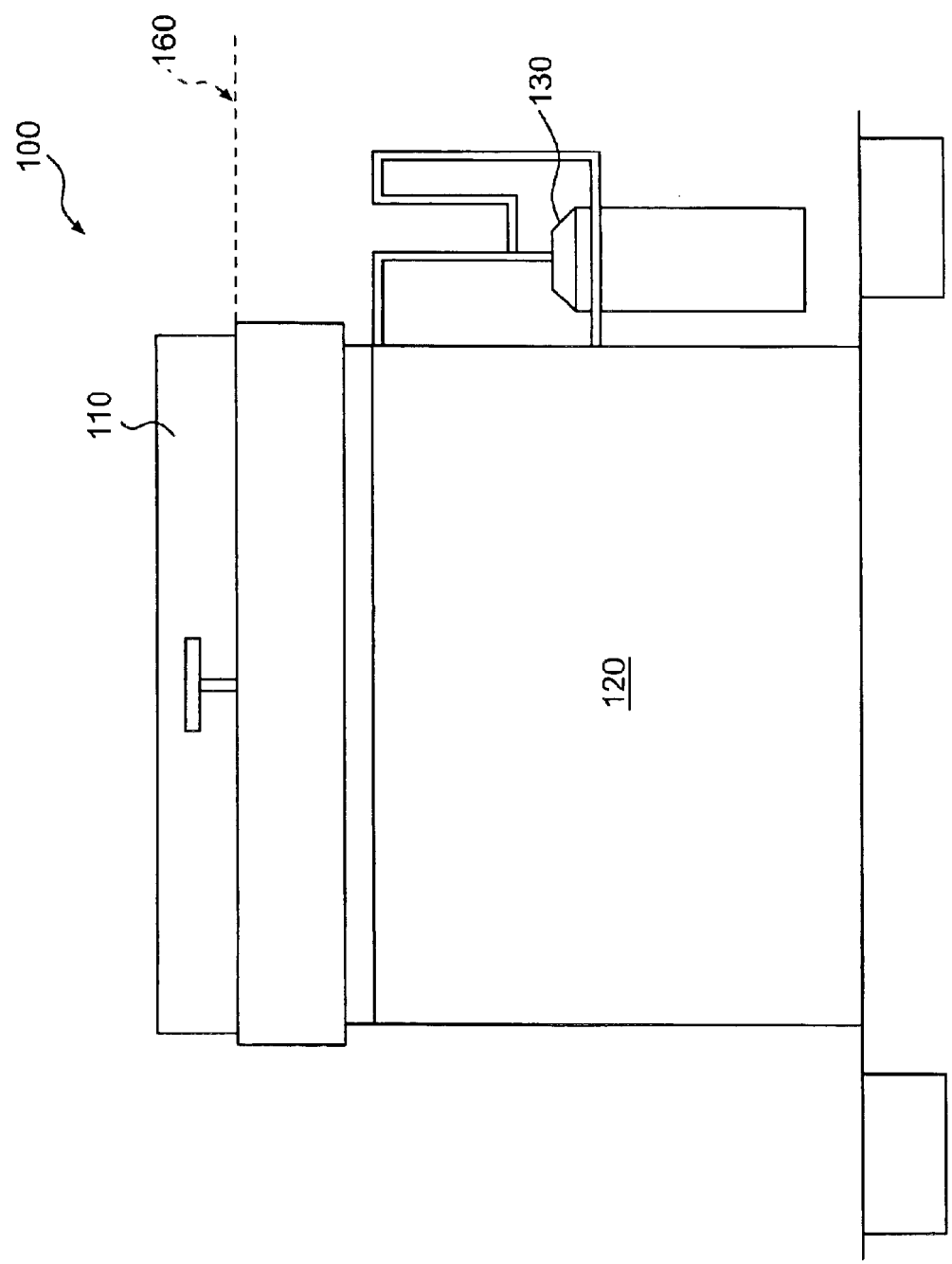
FIG. 4 illustrates a front view of the exemplary inward opening oven intake of FIG. 1.

FIG. 4 illustrates a front view of the exemplary inward opening oven intake 100 shown with the intake duct 120 and the inward opening intake flap 110. The inward opening intake flap 110 opens at a flap angle 150 into the GC oven 210 near the bottom of the GC oven (line 160). The oven intake 100 also includes a solenoid 130 with spring return to be used as a switch or control for the inward opening intake flap 110. As noted above, the solenoid 130 drives the mechanics connected to the inward opening intake flap 110 to adjust the opening angle of the inward opening intake flap 110.

Figure 5:
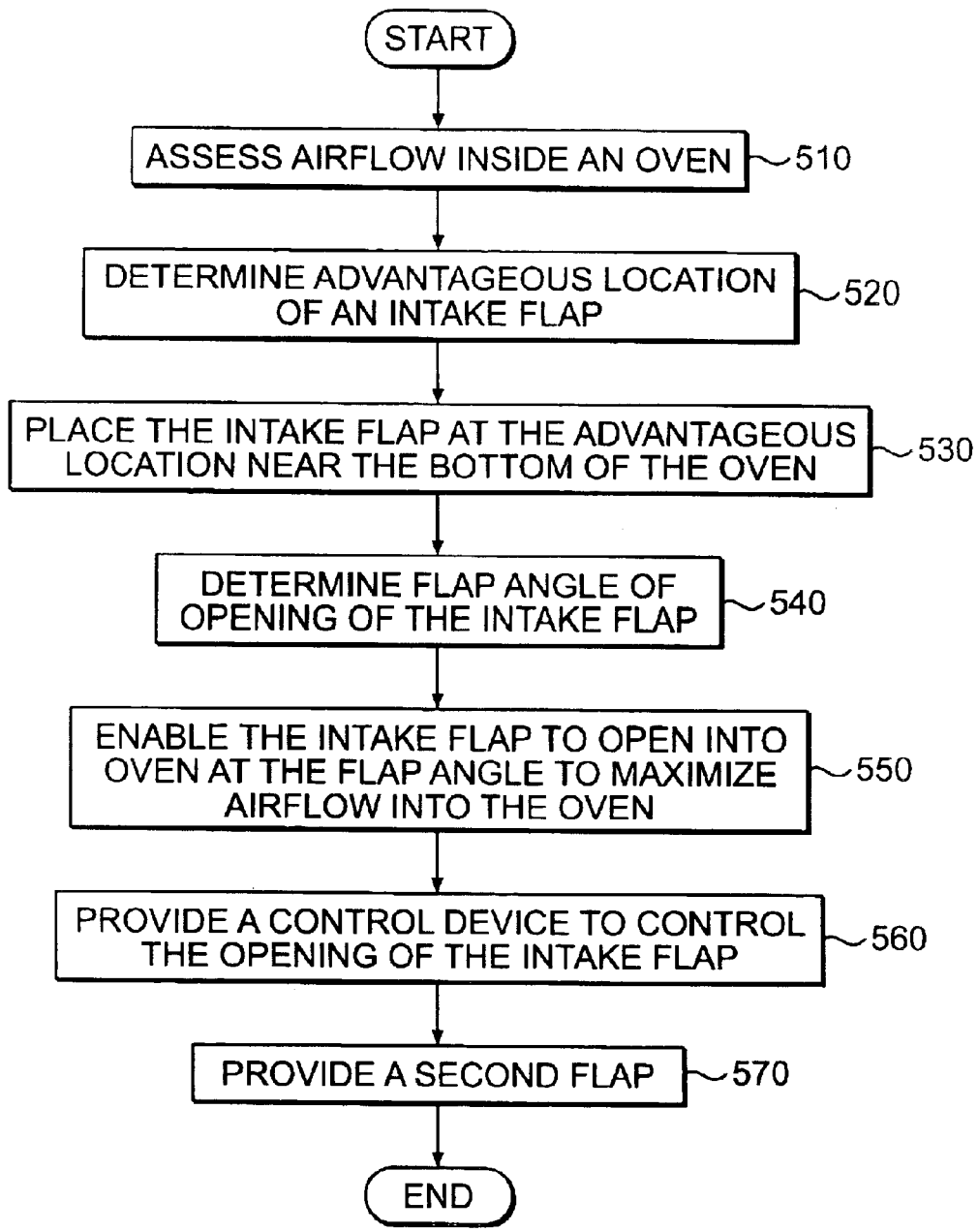
FIG. 5 is a flow chart illustrating an exemplary method for providing an inward opening oven intake for a GC oven.

FIG. 5 is a flow chart illustrating an exemplary method for providing an inward opening oven intake for a GC oven 210. After assessing the airflow 250 inside the GC oven 210 (block 510), the method determines an advantageous location for the inward opening intake flap 110 in the GC oven 210 (block 520). The method places the inward opening intake flap 110 at the advantageous location near the bottom of the GC oven 210 (block 530). Next, the method determines a flap opening angle 150 of the inward opening intake flap 110 based on the angle of the airflow 250 in the GC oven 210 flowing past the region where the inward opening intake flap 110 is located (block 540). The method enables the inward opening intake flap 110 to open into the GC oven 210 at a flap angle 150 to maximize the airflow flowing into the GC oven 210 from the opening (block 550). Cooling fans 140 may be used to produce the airflow. The method may also provide a control device to control the flap angle 150 (block 560). One embodiment is a solenoid 130 that controls and adjusts the opening angle of the inward opening intake flap 110. The method may also provide a second flap 115 to create a layer of air insulation 170 between the GC oven 210 and the cooling fans 140 (block 570).

While the system and method for providing an inward opening oven intake for a GC oven have been described in connection with an exemplary embodiment, those skilled in the art will understand that many modifications in light of these teachings are possible, and this application is intended to cover variations thereof.

What is claimed is:

1. An air intake for an oven, the oven having an inside and an outside comprising:

an intake duct; and a movable intake flap, operably connected to the intake duct, having a closed and an open orientation, the intake flap positioned so that when the intake flap is in the open orientation, more of the intake flap is located on the inside of the oven than on the outside of the oven, and in the open orientation, the intake flap is open into the oven at a flap angle that creates a low-pressure region to draw airflow into the oven from the intake duct.

2. The air intake of claim 1, wherein when the intake flap is in the open orientation, all of the intake flap is located on the inside of the oven.

3. The air intake of claim 1, wherein the oven is a gas chromatographic oven and wherein the intake duct is positioned beneath an oven and the intake duct includes one or more cooling fans so that when the intake flap is open airflow is drawn from the one or more cooling fans.

4. The air intake of claim 3, wherein the intake flap directs an airflow originating from the one or more cooling fans to approximate a direction of a second airflow originating from stirring fans inside the oven.

5. The air intake of claim 1, wherein the intake duct has a non-uniform cross-section.

6. The air intake of claim 1, wherein the intake flap is positioned at an advantageous location in the oven, and wherein the advantageous location is determined based on an assessment of airflow inside the oven.

7. The air intake of claim 1, wherein the flap angle is determined based on an assessment of airflow inside the oven.

8. The inward opening oven intake of claim 1, further comprising a second flap connected to the intake flap through a linkage system.

9. The inward opening oven intake of claim 8, further comprising a solenoid that controls the intake flap and the second flap, wherein the intake flap opens at the flap angle when the second flap opens at a second angle.

10. The inward opening oven intake of claim 8, wherein the flap angle and the second angle are pre-defined.

11. The inward opening oven intake of claim 8, wherein the intake flap and the second flap are controlled by a stepper motor.

12. The inward opening oven intake of claim 8, wherein the intake flap and the second flap are controlled by a proportional control device.

13. The inward opening oven intake of claim 9, wherein the solenoid enables the intake flap to automatically snap shut during a power loss.

14. The inward opening oven intake of claim 1, wherein the flap angle is an angle between 0° to 90°.

15. A method for providing an inward opening oven intake for a gas chromatographic oven, comprising:

assessing an airflow inside an oven;

determining an advantageous location for an intake flap;

placing the intake flap at the advantageous location near a bottom of the oven;

determining a flap angle of an opening of the intake flap;

enabling the intake flap to open into the oven at the flap angle to create a low-pressure region to draw airflow into the oven from one or more cooling fans.

16. The method of claim 15, further comprising enabling the intake flap to open into the oven at the flap angle to direct an airflow originating from one or more cooling fans to approximate a direction of a second airflow originating from stirring fans inside the oven.

17. The method of claim 15, wherein the determining the flap angle step includes determining the flap angle based on an assessment of an airflow inside the oven and a second angle of a second airflow flowing past an region where the intake flap is located.

18. A system for providing an inward opening oven intake for a gas chromatographic oven, comprising:

an intake duct positioned beneath an oven, the intake duct having one or more cooling fans; and an intake flap positioned at an advantageous location near a bottom of the oven, the intake flap opening into the oven at a flap angle to direct an airflow originating from the one or more cooling fans to approximate a direction of a second airflow originating from stirring fans inside the oven.

19. The system of claim 18, wherein the flap angle is determined based on an assessment of an airflow inside the oven.

20. The system of claim 18, further comprising a solenoid that controls movement of the intake flap and enables the intake flap to automatically snap shut during a power loss.

* * * * *